United States Patent
Salsman

(10) Patent No.: US 9,347,962 B2
(45) Date of Patent: May 24, 2016

(54) HANDHELD DIAGNOSTIC SYSTEM WITH CHIP-SCALE MICROSCOPE AND AUTOMATED IMAGE CAPTURE MECHANISM

(71) Applicant: NANOSCOPIA (CAYMAN), INC., Cayman Islands (KY)

(72) Inventor: Kenneth Edward Salsman, Pleasanton, CA (US)

(73) Assignee: NanoScopia (Cayman), Inc., Grand Cayman (KY)

( * ) Notice: Subject to any disclaimer, the term of this patent is extended or adjusted under 35 U.S.C. 154(b) by 130 days.

(21) Appl. No.: 13/959,304

(22) Filed: Aug. 5, 2013

(65) Prior Publication Data

US 2015/0037786 A1 Feb. 5, 2015

(51) Int. Cl.
| | | |
|---|---|---|
| *G01N 35/00* | (2006.01) | |
| *G01N 35/04* | (2006.01) | |
| *G02B 21/00* | (2006.01) | |
| *B01L 3/00* | (2006.01) | |

(52) U.S. Cl.
CPC .......... *G01N 35/00* (2013.01); *B01L 3/502715* (2013.01); *G01N 35/00732* (2013.01); *G01N 35/04* (2013.01); *G02B 21/0008* (2013.01); *B01L 2200/025* (2013.01); *B01L 2200/0647* (2013.01); *B01L 2200/10* (2013.01); *B01L 2200/16* (2013.01); *B01L 2300/027* (2013.01); *B01L 2300/0654* (2013.01); *G01N 2035/00772* (2013.01); *G01N 2035/00801* (2013.01); *G01N 2035/0436* (2013.01); *Y10T 436/25* (2015.01)

(58) Field of Classification Search
CPC ............ G01N 35/00; G01N 35/00732; G01N 2035/0436; G01N 2035/00772; G01N 35/04; G01N 2035/00801
See application file for complete search history.

(56) References Cited

U.S. PATENT DOCUMENTS

| | | | |
|---|---|---|---|
| 6,132,685 A * | 10/2000 | Kercso et al. ................. | 422/566 |
| 6,326,083 B1 | 12/2001 | Yang et al. | |
| 6,630,205 B2 | 10/2003 | Brueck et al. | |
| 6,723,290 B1 | 4/2004 | Wardlaw | |
| 6,866,823 B2 | 3/2005 | Wardlaw | |
| 7,435,578 B2 | 10/2008 | Wikswo et al. | |
| 7,466,409 B2 | 12/2008 | Scherer et al. | |
| 7,524,459 B2 | 4/2009 | Adams et al. | |
| 7,751,048 B2 | 7/2010 | Yang et al. | |
| 8,105,849 B2 | 1/2012 | McDevitt et al. | |
| 8,465,698 B2 | 6/2013 | Yamakawa et al. | |
| 8,717,556 B2 * | 5/2014 | Salsman ........................ | 356/246 |
| 2003/0138819 A1 | 7/2003 | Gong et al. | |
| 2003/0235924 A1 | 12/2003 | Adams et al. | |
| 2004/0115731 A1 | 6/2004 | Hansen et al. | |
| 2004/0151629 A1 | 8/2004 | Pease et al. | |
| 2004/0165778 A1 | 8/2004 | Cartlidge et al. | |
| 2007/0003443 A1 | 1/2007 | Sandell et al. | |
| 2007/0292941 A1 | 12/2007 | Handique et al. | |
| 2009/0130745 A1 | 5/2009 | Williams et al. | |
| 2009/0147918 A1 * | 6/2009 | Fowler et al. ................. | 378/73 |
| 2010/0186524 A1 | 7/2010 | Ariessohn et al. | |
| 2011/0181884 A1 | 7/2011 | Cui et al. | |
| 2011/0311394 A1 | 12/2011 | Worsman et al. | |
| 2012/0008848 A1 | 1/2012 | Beck | |
| 2012/0044341 A1 | 2/2012 | Stith et al. | |
| 2012/0045786 A1 | 2/2012 | Stith | |
| 2012/0218379 A1 | 8/2012 | Ozcan et al. | |

FOREIGN PATENT DOCUMENTS

| | | |
|---|---|---|
| EP | 1442787 | 8/2004 |
| EP | 2258951 | 12/2010 |
| WO | 2009111573 | 9/2009 |
| WO | 2011073410 | 6/2011 |

OTHER PUBLICATIONS

International Search Report dated Nov. 13, 2014, for PCT/US2014/049226.
Good et al., "An Effervescent Reaction Micropump for Portable Microfluidic Systems", Lab on a Chip, Royal Society of Chemistry, vol. 6, No. 5, Jan. 1, 2006 (pp. 659-666).

* cited by examiner

*Primary Examiner* — Shanon A Foley
(74) *Attorney, Agent, or Firm* — Shay Glenn LLP

(57) ABSTRACT

A handheld diagnostic system may include a disposable sample holder for receiving and containing a biological sample and an analysis module having a chip-scale microscope. The sample holder may include a plurality of uniformly spaced tick marks. The analysis module may include a sensor for detecting the tick marks as the sample holder is inserted into the analysis module. The chip-scale microscope may include an image sensor for capturing images of the sample. Each time the sensor detects a tick mark, control circuitry may issue a control signal to the image sensor to capture an image of the biological sample. This type of automated image capture mechanism ensures that images are captured at a uniform spatial distribution even when the sample holder is inserted into the analysis module at variable speed. The analysis module may transmit sample imaging data to a portable electronic device.

9 Claims, 6 Drawing Sheets

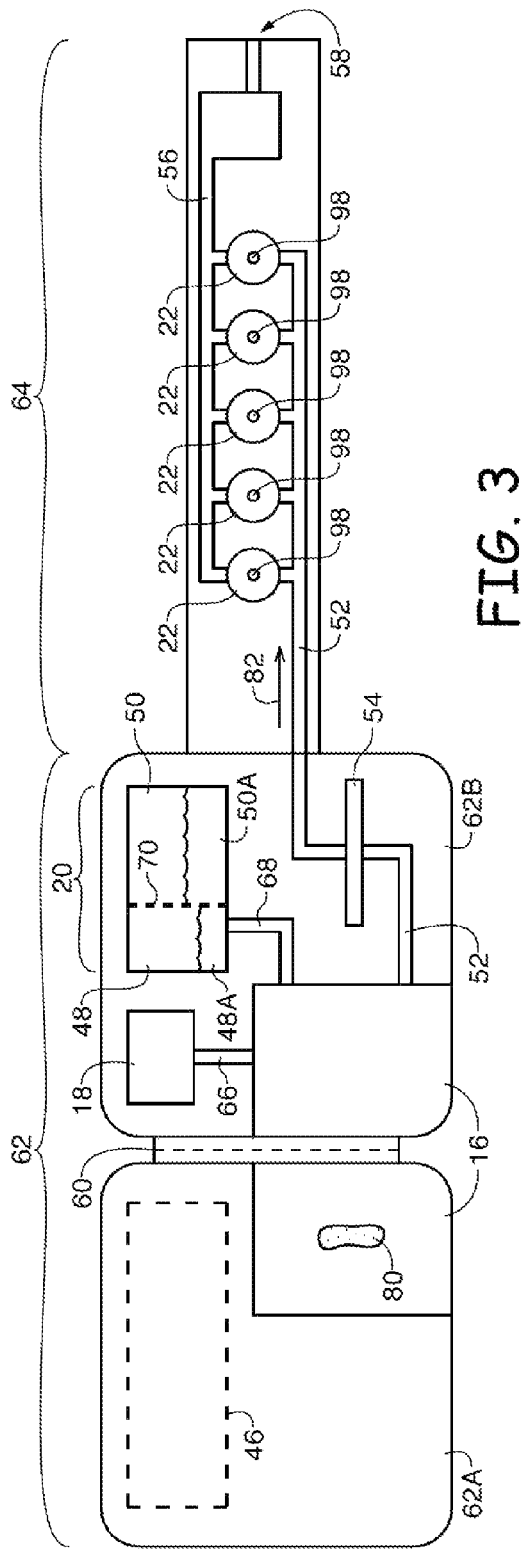
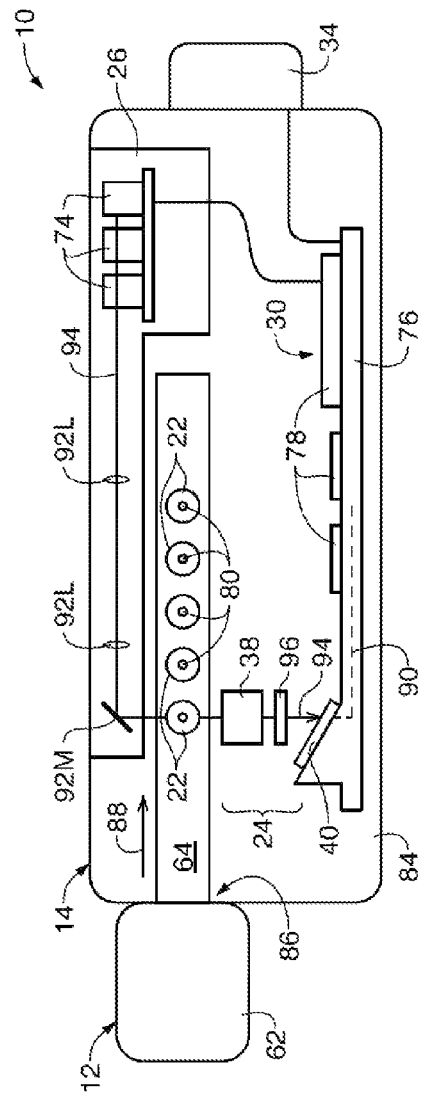

HANDHELD DIAGNOSTIC SYSTEM WITH CHIP-SCALE MICROSCOPE AND AUTOMATED IMAGE CAPTURE MECHANISM

BACKGROUND

This relates generally to diagnostic systems and, more particularly, to handheld diagnostic systems with disposable sample holders and chip-scale microscopes.

Conventional diagnostic systems often require external wet chemistry (e.g., performed in a wet laboratory) and are typically only operated by trained personnel having professional expertise. Conventional diagnostic systems are also limited in their abilities to perform multiple tests simultaneously on a single sample.

Because of these factors, conventional diagnostic systems and microscopic imaging systems are typically non-portable, have high cost-per-test, and are unavailable or inconvenient for patients and care providers to use.

Moreover, microscopic imaging is traditionally limited to a very narrow depth of field that shrinks as the magnification increases. Scanning techniques are sometimes used to build a large depth of field image by combining multiple image frames at various focal lengths or to construct detailed images by stacking frames that have a focal plane at an angle to the sample surface.

Scanning techniques require precise control of the motion of the sample in order to accurately position the imaging frames. Typical systems achieve this level of control using step and repeat image capture and calibrated motions stages. Complex sample stage mechanisms and drive systems add significant weight, size, and cost to a system and can negatively affect its reliability and power requirements.

It would therefore be desirable to be able to provide improved diagnostic systems with microscopic imaging.

BRIEF DESCRIPTION OF THE DRAWINGS

FIG. 3 is a cross-sectional side view of an illustrative sample holder in accordance with an embodiment of the present invention.

FIG. 4 is a cross-sectional top view of an illustrative handheld diagnostic system having a sample holder and an analysis module with a chip-scale microscope in accordance with an embodiment of the present invention.

DETAILED DESCRIPTION

Figure 1:
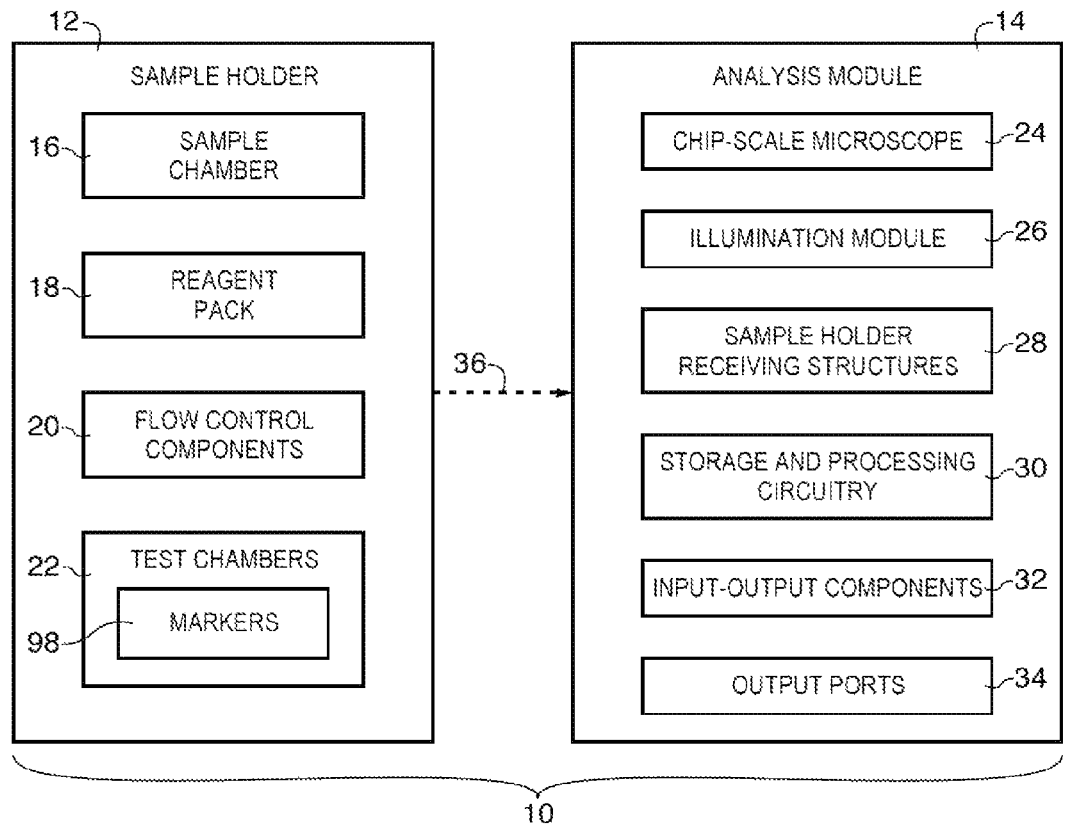
FIG. 1 is a diagram of an illustrative diagnostic system having a sample holder and an analysis module for capturing and analyzing magnified images of cells and other biological specimens in accordance with an embodiment of the present invention.

Systems such as diagnostic systems may be provided with a disposable sample holder and a handheld, portable analysis module having a chip-scale microscope. The disposable sample holder may have internal flow control structures and mechanisms for moving fluids, samples, particles, reactants and/or reagents from one part of the system to another. The sample holder may have multiple test chambers for performing multiple tests simultaneously on a single sample. The sample holder may be configured to protect the sample from contamination, to protect the user from exposure to infectious agents, and to provide the ability to add reagents to the sample. The analysis module may have an opening that is configured to receive the sample holder. The chip-scale microscope may capture magnified images of the sample using the chip-scale microscope as the sample holder is inserted into the analysis module.

The handheld analysis module may be configured to connect with and provide sample analysis information to an electronic device such as a cellular telephone, a laptop, a tablet computer, or other portable computing device. The electronic device may display images captured by the analysis module, may perform additional image analysis, and/or may control specific functions within the analysis module. The analysis module and/or the electronic device may be configured to communicate sample analysis information from the analysis module over a communications network.

The chip-scale microscope may include an image sensor formed from complementary metal-oxide-semiconductor (CMOS) technology or other suitable image sensor integrated circuit technology. The chip-scale microscope may also include optics for focusing light from the sample onto the image sensor. An interchangeable illumination module in the analysis module may be used to illuminate the sample with a desired light source.

This type of diagnostic system may be used to analyze biological materials, bio-chemical materials, chemical materials, and/or other types of materials, and may be configured to perform spectral imaging operations such as narrow band imaging, multiple discrete band imaging, and fluorescence imaging (e.g., bio-fluorescence imaging as may be used in molecular analysis of biological samples).

The diagnostic system may be capable of performing medically viable diagnostics without requiring external wet chemistry or laboratory-trained personnel, may operate at low cost-per-test, and may be capable of operation in a variety of field environments (e.g., environments in which modern medical facilities are not available or are inconvenient).

The chip-scale microscope may be configured to capture spatially uniform imaging frames using an automated image capture mechanism. The automated image capture mechanism may be based on a sensor that detects when the next imaging frame should be captured. For example, the sample holder may include a series of uniformly spaced markings. When a user inserts the sample holder into the analysis module, the series of uniformly spaced markings may be detected by a sensor in the analysis module. Upon detecting one of the markings, a control signal may be issued to capture an imaging frame using the chip-scale microscope. This type of automated triggering ensures that the chip-scale microscope captures imaging frames at a uniform spatial distribution even when the sample is moving and even when the sample holder is inserted manually into the analysis module at variable speed. The sensor may be a photodiode that is separate from the image sensor in the chip-scale microscope or may formed from an edge of the image sensor itself in the chip-scale microscope.

A system of the type that may be used to image and otherwise evaluate cells and other samples such as biological specimens is shown in FIG. 1. As shown in FIG. 1, system 10 may include a sample holder such as sample holder 12 and an analysis module such as analysis module 14. As indicated by arrow 36, analysis module 14 may be configured to receive sample holder 12. Analysis module 14 may be configured to image and analyze samples in different types of disposable sample holders such as sample holder 12.

Sample holder 12 and analysis module 14 may be relatively small in size. For example, sample holder 12 may have a maximum lateral width of less than one inch, less than half of one inch, less than one quarter of one inch, less than four inches, or less than ten inches. Analysis module 14 may have a maximum lateral length of less than three inches, less than two inches, less than one inch, less than four inches, or less than ten inches. Sample holder 12 and analysis module 14 may each be small enough to fit in a user's hand, if desired.

Sample holder 12 may have a sample chamber such as sample chamber 16, one or more reagent packs such as reagent pack 18, flow control components such as flow control components 20, and one or more test chambers such as test chambers 22.

Sample chamber 16 may be configured to receive a sample from a user of system 10. For example, a user may place a swab on which a sample has been collected into sample chamber 16, or a user may place a sample on its own (e.g., a blood sample that has been collected with a lancet) into sample chamber 16. The sample may be a biological sample including cells or other biological elements. If desired, system 10 may be used to analyze and capture high-magnification images of other types of samples (e.g., other biological specimen or other particles or materials). Arrangements in which system 10 is used to image cells are sometimes described herein as an example.

In some situations, it may be desirable to mix the sample with a reagent. Examples of reagents that may be introduced to the sample and allowed to interact with the sample include diluents (e.g., fluids such as ionic fluids), dyes (e.g., fluorescent dyes), or other chemical compounds, biological agents such as antigens, antibodies (e.g., antibodies with dye), phosphors, electrolytes, analyte-specific antibodies, etc. Reagent pack 18 may be used to contain reagents until they are introduced to the sample in sample chamber 16. If desired, there may be one, two, or more than two reagent packs within a single sample holder.

Flow control components 20 may be used to control the flow of a sample within sample holder 12 without requiring electrical power. Flow control components 20 may, for example, include one or more compartments of chemicals configured to react with each other and produce gas which then forces the sample through a channel in the sample holder and distributes portions of the sample into respective test chambers 22 in sample holder 12. For example, flow control components 20 may include a pack or compartment of acetic acid (vinegar) and a pack or compartment of sodium bicarbonate (baking soda). When combined, the sodium bicarbonate and acetic acid may produce carbon dioxide gas which then pushes the sample through the channel in a smooth, continuous, and predictable manner. This type of configuration is advantageous in that it does not require electrical power and also avoids the abrupt jerking of the sample which occurs when a pump is used to control the flow of a sample. However, if desired, other types of flow control structures such as one or more pumps may be used to move the sample from one location in sample holder 12 to another location in sample holder 12.

Test chambers 22 may each be configured to receive a portion of the sample from sample chamber 16. Each test chamber 22 may, for example, contain a different marker such as marker 98 configured to tag a specific chain of DNA, RNA, or protein. For example, markers 98 in test chambers 22 may be configured to locate and mark specific nucleic acids or proteins (e.g., nucleic acids or proteins associated with a bacterium, virus, poison, fungus, parasite, etc.) in the sample with specific colors (e.g., using stains, dyes, and/or fluorescent tagging). Each marker 98 in each test chamber 22 may be used to identify a different bacteria, virus, poison, fungus, or parasite in a single sample, thereby providing system 10 with the ability to perform multiple tests on a single sample simultaneously. There may be one, two, three, four, five, six, or more than six test chambers 22 within sample holder 12. Illustrative examples of substances or structures that may be identified using system 10 include *S. aureus*, Coagulase-negative staphylococci (CNS), *E. faecalis*, *E. faecium* and other *Enterococci*, *E. coli*, *K. pneumoniae*, *P. aeruginosa*, *C. albicans*, *C. parapsilosis*, *C. tropicalis*, *C. glabrata*, *C. krusei*, *Listeria*, foot-and-mouth disease virus, Methicillin-resistant *Staphylococcus aureus* (MRSA), and malaria parasites such as *P. falciparum* and other malaria parasites.

In one suitable embodiment, markers 98 may be configured to tag structures within the sample using a process referred to as immunolabeling. In this type of configuration, markers 98 may include tagged conjugate antibodies that are configured to attach themselves to locations where the corresponding target antigen is found. The conjugate antibodies may be tagged with a fluorescent compound, gold beads, an epitope tag, or an enzyme that produces a colored compound.

In another suitable embodiment, markers 98 may be configured to attach fluorophores to oligonucleotides complementary to the target RNA molecules (as an example).

Reagents and markers in sample holder 12 can be stored in active or in freeze-dried form. Substances stored in freeze-dried form may be activated with the addition of water and/or other reagents.

Sample holder 12 allows the chemistry required for sample processing and the sample itself to be sealed and safely contained once acquired and allows for the processing to be automated within a low-cost structure. If desired, sample holder 12 may be disposed with the sample when the sample analysis is complete or may be used to keep the sample in a safe, contained enclosure until further analysis can be performed in a fully-equipped laboratory. The chemistry, sample processing, and internal structure of a given sample holder may be customized depending on the type of test(s) or analysis being performed. Sample holders 12 may be provided with a common external mechanical structure so that analysis modules 14 are compatible with many different types of sample holders 12, each of which is designed for performing a specific set of tests. Sample holder 12 may be produced inexpensively in high volume and may be disposed of after a single use (if desired).

Analysis module 14 may include chip-scale microscope 24, illumination module 26, sample holder receiving structures 28, storage and processing circuitry 30, input-output components 32, and output ports 34.

Chip-scale microscope 24 may include an image sensor for imaging samples within sample holder 12 and optics such as one or more lenses and/or mirrors for focusing light from the sample onto the image sensor.

Illumination module 26 may include one or more light sources (e.g., one or more light-emitting diodes, arc lamps, lasers, or other suitable type of light source) for illuminating the sample in sample holder 12. Illumination module 26 may also include one or more optical structures such as mirrors, gratings, and/or condenser lenses for focusing light from the light source onto the sample.

Analysis module 14 may include a housing having sample holding receiving structures 28 for receiving sample holder 12. Sample holder receiving structures 28 may include an opening into which sample holder 12 is inserted. The opening may be provided with guide rails or other alignment structures to facilitate insertion of sample holder 12 into analysis module 14. If desired, sample holder receiving structures 28 may include structures for controlling the rate of insertion of sample holder 12 into analysis module 14. For example, the opening into which sample holder 12 is inserted may include a pattern of gears or other structures configured to mate with a corresponding pattern of gears on an external surface of sample holder 12. Such structures may be used to ensure that the rate at which sample holder 12 is guided into analysis module 14 is kept constant or within a given range (if desired). Chip-sale microscope 24 may capture images of the sample as sample holder 12 is being inserted into analysis module 14.

Storage and processing circuitry 30 may include volatile memory (e.g., static or dynamic random-access memory), non-volatile memory (e.g., flash memory), microprocessors, integrated circuits, printed circuit boards, or other circuitry. Storage and processing circuitry 30 may be used for storing, processing, and analyzing image data captured using chip-scale microscope 24, and/or for operating components such as illumination module 26 and input-output components 32.

Storage and processing circuitry 30 may include communications circuitry such as circuitry coupled to output ports 34. Storage and processing circuitry 30 may include wireless communications circuitry for conveying data such as image data, sample analysis information, diagnosis information, etc. to external equipment such as a computer, a handheld electronic device, a cellular telephone, a network router, a network antenna, etc. For example, wireless communications circuitry associated with circuitry 30 may be configured to transmit and/or receive data at WiFi® frequencies (e.g., 2.4 GHz and 5 GHz), Bluetooth® frequencies (e.g., 2.4 GHz), cellular telephone frequencies (e.g., 85-MHz, 900 MHz, 1800 MHz, 1900 MHz, and 2100 MHz), or other frequencies.

Output ports 34 may include one or more universal serial bus (USB) ports, serial ports, audio ports, video ports, etc. coupled to storage and processing circuitry 30.

Data that may be transmitted using ports 34 or wireless communications circuitry associated with circuitry 30 may include identification data associated with a particular analysis module, identification data associated with a particular sample holder, identification data associated with a sample, geographic location data associated with the location of the analysis module, sample analysis information resulting from analysis of a sample within sample holder 12, raw and/or processed imaging data obtained using chip-scale microscope 24, and/or other information. Sample analysis information may, for example, include a medical diagnosis or an identification of which substances or structures were found to be present or absent in the sample.

Illustrative examples of procedures that may be performed using system 10 include whole blood cell analysis, cell counting, Complete Blood Count (CBC), nucleic acid amplification, PNA-FISH® bacterial testing, antigen and antibody infectious disease detection, and other tests. Because system 10 is handheld and portable, such tests may be performed in locations where laboratory facilities are unavailable or inconvenient for a user.

System 10 may provide a user with the ability to interact with analysis module 14. User interactions may include inputting identification information (e.g., information identifying a sample, a sample donor, a geographic location, etc.) and obtaining output information (e.g., reading the result of an analysis performed using chip-scale microscope 24). To implement these interactions, analysis module 14 may have input-output components 32 such as keypads, virtual keypads, buttons, displays, or other suitable input-output components. Input-output components 32 may include circuitry coupled to one or more output ports such as output port 34 mounted in a housing structure.

Figure 2:
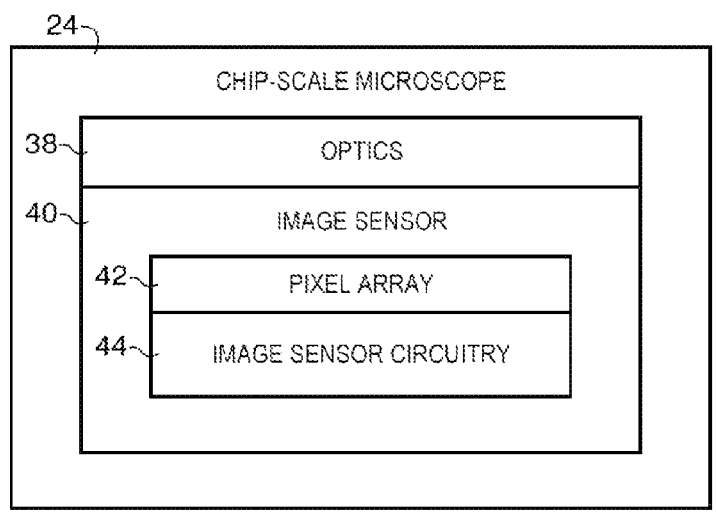
FIG. 2 is a diagram of an illustrative chip-scale microscope in accordance with an embodiment of the present invention.

An illustrative configuration for chip-scale microscope 24 is shown in FIG. 2. As shown in FIG. 2, chip-scale microscope 24 may include optics such as optics 38 and an image sensor (sometimes referred to as an imager) such as image sensor 40. Image sensor 40 may include an array of image pixels such as pixel array 42 and image sensor circuitry such as image sensor circuitry 44. Image sensor circuitry 44 may include row control circuitry, column readout circuitry, analog-to-digital conversion circuitry, and other circuitry associated with capturing raw data using image pixel array 42 of image sensor 40. Circuitry 30 of FIG. 1 may, for example, be used to control imaging functions performed using chip-scale microscope 24.

Optics 38 (sometimes referred to as microscope objective 38) may include optical elements for gathering light from the sample in sample holder 12 and focusing the light onto pixel array 42 of image sensor 40. Optics 38 may include one or more objective lenses, one or more mirrors, one or more layers of glass, and/or other optical structures for focusing light from the sample onto image sensor 40. Optics 38 may, for example, be interposed between the sample (when sample holder 12 is inserted into analysis module 14) and image sensor 40. Optics 38 may be characterized by a magnification of 1000×, 400×, 200×, or other suitable magnification; may be characterized by a numerical aperture of less than 0.5, less than 1.0, less than 1.5, or greater than 1.5; and may be characterized by a working distance of 5 mm, greater than 5 mm, less than 5 mm, less than 10 mm, or greater than 10 mm. Chip-scale microscope 24 may be configured to achieve a depth of field of about 125 microns, about 130 microns, about 120 microns, about 100 microns, less than 100 microns, greater than 100 microns, or greater than 120 microns.

Microscope objective 38 may, if desired, operate with an air medium, thereby eliminating the need for an immersion liquid between the front lens element and the sample. Chip-scale microscope 24 may be equipped to obtain volumetric data using the automatic focus functionality of image sensor 40 without requiring an automated stage.

A cross-sectional top view of sample holder 12 is shown in FIG. 3. As shown in FIG. 3, sample holder 12 may include a first portion such as sample-receiving portion 62, and a second portion such as sample imaging portion 64.

Sample-receiving portion 62 may include reagent pack 18, flow control components 20, and sample chamber 16. As described in connection with FIG. 1, reagent pack 18 may be used to contain reagents until they are introduced to the sample in sample chamber 16. Initially, reagent pack 18 may be sealed from sample chamber 16. Upon breaking the seal, reagents in reagent pack 18 may be allowed to interact with a sample such as sample 80 in sample chamber 16 via path 66.

Flow control components 20 may provide a sample distribution mechanism for distributing portions of sample 80 in sample chamber 16 to respective test chambers 22. Flow control components 20 may be implemented as a gas generating component having two adjacent chambers 48 and 50. Chamber 48 may contain a first reactant such as liquid reactant 48A (e.g., acetic acid). Chamber 50 may contain a second reactant such as solid or powder reactant 50A (e.g., sodium bicarbonate). First and second reactants 48A and 50A may be selected to be stable chemicals (e.g., acetic acid (vinegar) and sodium bicarbonate (baking soda), respectively) that generate a gas such as carbon dioxide when mixed.

Chambers 48 and 50 may initially be separated by structural member 70 (e.g., a plastic seal). When seal 70 is punctured or otherwise broken, chemical reactants 48A and 50A may be allowed to interact and a chemical reaction may occur, leading to the release of a significant volume of gas (e.g., carbon dioxide). The gas produced may provide pressure to chamber 16 via path 68, which may in turn move sample 80 in sample chamber 16 through channel 52 in direction 82. Portions of sample 80 may be distributed to respective test chambers 22 in sample imaging portion 64. If desired, a particle filter such as particle filter 54 may be configured to filter sample 80 to prevent certain substances or structures from passing through channel 52 to sample imaging portion 64.

Each test chamber 22 may be coupled to vent line 56. Vent line 56 may allow air to escape via exit port 58 and may be used in regulating the flow of air and the movement of sample 80, if desired.

If desired, other sample distribution mechanisms may be employed to distribute sample 80 in sample chamber 16 to test chambers 22. The use of sodium bicarbonate and acetic acid is merely.

Sample-receiving portion 62 may have a clamshell shape with first and second portions 62A and 62B connected by a bendable joint such as bendable joint 60. With this type of configuration, sample-receiving portion 62 of sample holder 12 may be configurable in open and closed positions. In the open configuration (as shown in FIG. 3), compartments within sample-receiving portion 62 may be sealed. For example, reagent pack 18 may be sealed and compartments 48 and 50 may be sealed and separated from each other. While sample-receiving portion 62 is open, a user may place a sample into sample chamber 16 and may then close sample-receiving portion 62 by bending sample-receiving portion 62 at bendable portion 60. Upon closing sample-receiving portion 62, a protrusion such as protrusion 46 (e.g., a structure having one or more sharp edges) within portion 62 may puncture reagent pack 18 and seal 70, thereby allowing reagents in reagent pack 18 to interact with the sample in sample chamber 16 while also allowing reactants 48A and 50A in compartments 48 and 50 to interact with each other. Sample 80 is mixed with reagents in reagent pack 18 and is moved through channel 52 to test chambers 22. With this type of configuration, the appropriate chemistry and sample processing may automatically occur within sample holder 12 by merely closing sample-receiving portion 62 after placing sample 80 in sample chamber 16.

If desired, sample chamber 16 may include a permeable or semi-permeable cover such as a neoprene membrane through which a needle may be inserted (as an example).

As described in connection with FIG. 1, each test chamber 22 in sample holder 12 may contain a different marker for tagging a specific substance (e.g., via staining, dying, fluorescent tagging, etc.). As an example, one test chamber 22 may contain a marker for tagging foot-and-mouth disease virus, while another test chamber 22 may contain a marker for tagging Methicillin-resistant *Staphylococcus aureus* (MRSA). Because the sample is automatically distributed to chambers 22 by closing sample-receiving portion 62, the sample may automatically be tagged by different markers in chambers 22, without requiring external wet chemistry or laboratory-trained personnel. Moreover, by simultaneously tagging different portions of a single sample in sample holder 12 with different markers, different types of tests (e.g., tests for different types of bacteria, viruses, fungi, parasites, etc.) may be performed simultaneously on a single sample.

Sample holder 12 may be formed from plastic, glass, metal, carbon fiber and/or other fiber composites, ceramic, glass, wood, other materials, or combinations of any two or more of these materials. Sample imaging portion 64 may be designed for microscopic imaging (e.g., may be partially or fully transparent so that sample 80 in test chambers 22 may be illuminated for microscopic imaging).

FIG. 4 is a cross-sectional top view of system 10 in which sample holder 12 has been inserted into analysis module 14. As shown in FIG. 4, analysis module 14 may include a housing such as housing 84 having an opening such as opening 86. Opening 86 may be have a shape that corresponds to the shape of sample imaging portion 64 of sample holder 12 so that sample imaging portion 64 of sample holder 12 may be inserted into analysis module 14. Sample holder 12 may be engaged with analysis module 14 by inserting sample imaging portion 64 of sample holder 12 into opening 86 in direction 88.

As shown in FIG. 4, output port 34 may be implemented as a USB connector for coupling module 14 to external equipment such as a computer, cell phone, laptop computer, tablet computer, etc. In addition to providing a means for communicating sample analysis information and/or sample imaging data from analysis module 14 to external electronic devices, output port 34 may also be configured to provide power to components within analysis module 14. For example, port 34 may include a power supply for providing power to illumination module 26, image sensor 40, and storage and processing circuitry 30. This is, however, merely illustrative. If desired, electrical components in analysis module 14 may receive power from an external power source.

Storage and processing circuitry 30 may be implemented using a printed circuit substrate such as printed circuit substrate 76, integrated circuits or other electrical components such as electrical components 78, and/or other circuitry in analysis module 14. Image sensor 40 may be coupled to printed circuit board 76 using an array of solder balls (e.g., a ball grid array) or may be coupled to printed circuit board 76 using other mounting techniques. Printed circuit board 76 may include metal traces 90 for electrically coupling image sensor 40 to other circuitry such as integrated circuit 78.

Lighting components 26 may be mounted in analysis module 14 so that light from lighting sources 74 passes through test chambers 22 of sample holder 12 during sample analysis operations. As described in connection with FIG. 1, illumination module 26 may include one or more light sources such as light sources 74 (e.g., one or more light-emitting diodes, arc lamps, lasers, or other suitable type of light source) for illuminating sample 80 in sample holder 12. Light sources 74 may be white light sources or may be configured to emit different colors of light. For example, light source 74 may be white light sources that are provided with different colored filters.

Illumination module 26 may include one or more optical structures such as lenses 92L mirror 92M for focusing light 94 from light source 74 onto sample 80. In response to control signals from control circuitry 30, light sources 74 may produce light 94 of a desired color and intensity. Light 94 may be directed through sample holder 12 (when sample holder 12 is inserted into analysis module 14) towards image sensor 40.

Illumination module 26 may be interchangeable so that different types of microscopy may be performed. For example, a first illumination module may be used to perform fluorescence microscopy using chip-scale microscope 24, and a second illumination module may be used to perform bright field microscopy using chip-scale microscope 24. When it is desired to change the type of microscopy being performed, the first illumination module may be removed from analysis module 14 and the second illumination module may be installed in its place (or vice versa).

Light 94 may pass through sample 80 and may be focused onto image sensor 40 using optics 38. As described in connection with FIG. 2, optics 38 may include one or more objective lenses, one or more mirrors, one or more layers of glass, and/or other optical structures for focusing light from sample 80 onto image sensor 40. If desired, one or more optical filters such as optical filter 96 may be interposed between optics 38 and image sensor 40. Like illumination module 26, optical filters in analysis module 14 such as optical filter 96 may be interchangeable so that different types of microscopy may be performed. Illustrative types of filters that may be used in analysis module 14 include longpass filters, colored and/or neutral density filters, absorptive filters, interference filters, dichroic filters, polarization filters, other suitable types of filters, or a combination of any two or more of these types of filters.

After a user injects or otherwise places a sample into test chamber 16 (FIG. 3) and closes sample-receiving portion 62, flow control components 20 may automatically be activated to distribute portions of sample 80 into respective test chambers 22 (as shown in FIG. 4). The user may then insert sample holder 12 into analysis module 14 by sliding sample imaging portion 64 of sample holder 12 into opening 86 of analysis module 14 in direction 88. As sample imaging portion 64 of sample holder 12 moves in direction 88 within cavity 86, each test chamber 22 may pass through light 94 and over image sensor 40. In the configuration shown in FIG. 4, for example, sample 80 in the rightmost chamber 22 will be the first to pass through light 94 over image sensor 40 and will therefore be the first specimen to be imaged with image sensor 40. As the user continues to push sample holder 12 into analysis module 14, sample 80 in the second chamber 22 from the right will pass through light 94 over image sensor 40 and will therefore be the second specimen to be imaged with image sensor 40. In this way, light 94 may successively illuminate sample 80 in each test chamber 22, and images may be successively captured of sample 80 in each chamber 22 as each chamber 22 is moved across the field of view of chip-scale microscope 24.

Analysis module 14 may include circuitry for automatically triggering each image capture operation as test chambers 22 move across image sensor 40.

Figure 5:
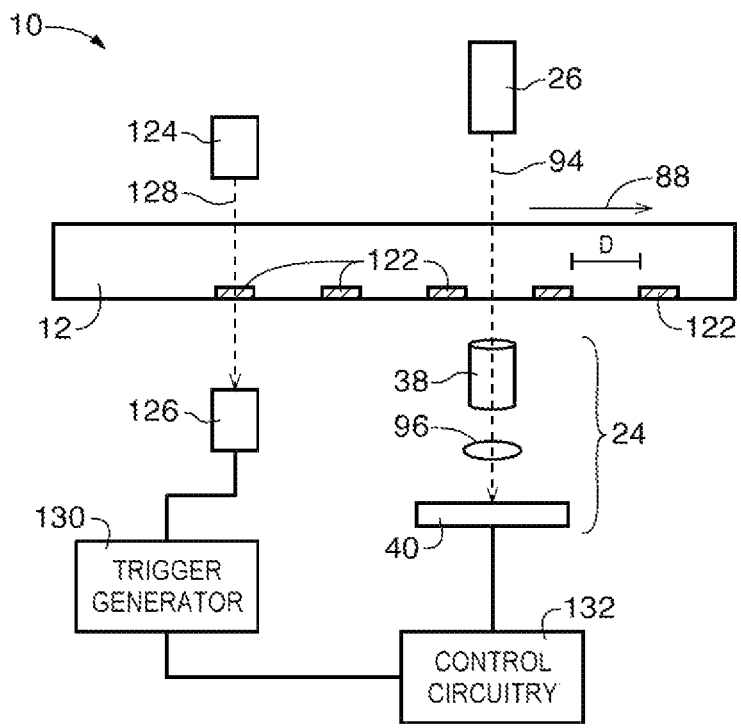
FIG. 5 is a diagram of an illustrative handheld diagnostic system that employs an automated image capture mechanism using a sensor and a series of reference markings on a sample holder in accordance with an embodiment of the present invention.

Sample imaging portion 64 of sample holder 12 may have uniformly spaced reference markings distributed along the length of sample imaging portion 64 (i.e., along the portion of sample holder 12 that is inserted into analysis module 14). Reference markings in sample holder 12 may be detected by a sensor in analysis module 14 and may be configured to trigger an automated image capture mechanism whereby chip-scale microscope 24 captures imaging frames at a uniform spatial distribution. FIG. 5 is a diagram of a portion of system 10 showing how system 10 may include a sensor for detecting reference markings on sample holder 12 for automatically triggering image capture operations as sample holder 12 is inserted into analysis module 14.

As shown in FIG. 5, sample holder 12 may have reference markings such as reference markings 122. There may be five, ten, fifteen, twenty, more than twenty, or less than twenty reference markings 122 on sample holder 12. Reference markings 122 may be separated from each other by a distance D. Analysis module 14 may include a sensor such as sensor 126 and a light source such as light source 124. Light source 124 (e.g., a light-emitting diode light source or other type of light source) may, for example, be formed as part of illumination module 26 or may be separate from illumination module 26. Sensor 126 and light source 124 may be aligned such that sensor 126 is configured to receive light 128 emitted by light source 124. Sensor 126 may include one or more photodiodes or other suitable type of light sensor.

Sensor 126 may be coupled to a trigger generator such as trigger generator 130 and control circuitry such as control circuitry 132. Control circuitry 132 and trigger generator 130 may, for example, form part of storage and processing circuitry 30 (FIG. 4). Control circuitry 132 may be coupled to image sensor 40 and may be configured to issue control signals to image sensor 40 based on signals received from sensor 126 via trigger generator 130.

As a user inserts sample holder 12 into analysis module 14 (e.g., in direction 88), sensor 126 may be configured to detect when reference markings 122 pass through light 128. Upon detecting one of reference markings 122, trigger generator 130 may generate a trigger signal for control circuitry 132, which may in turn issue control signals to image sensor 40 to capture an imaging frame. Thus, each time a reference marking 122 in sample holder 12 passes over sensor 126 in analysis module 14, image sensor 40 may capture an image of sample 80 in sample holder 12. This automated image capture mechanism ensures that imaging frames are captured at a uniform spatial distribution even when the sample is moving and even when the sample holder is inserted manually into the analysis module at variable speeds.

The distance D between reference markings 122 may be any suitable distance (e.g., 1 mm, 2 mm, 3 mm, 5 mm, less than 5 mm, or more than 5 mm). If desired, multiple imaging frames may be captured of each portion of sample 80 in each respective test chamber 22. Capturing multiple imaging frames of sample 80 at uniform spatial distribution may allow processing circuitry (e.g., processing circuitry 30) to build a large depth of field image of sample 80 by combining multiple imaging frames at different focal lengths; to construct a detailed image of sample 80 by stacking frames that have a focal plane at an angle to the sample surface, thereby providing a focal region that is larger than a single frame focal region; and to build images of large samples by stitching together multiple imaging frames that have a uniform spatial distribution.

Figure 6:
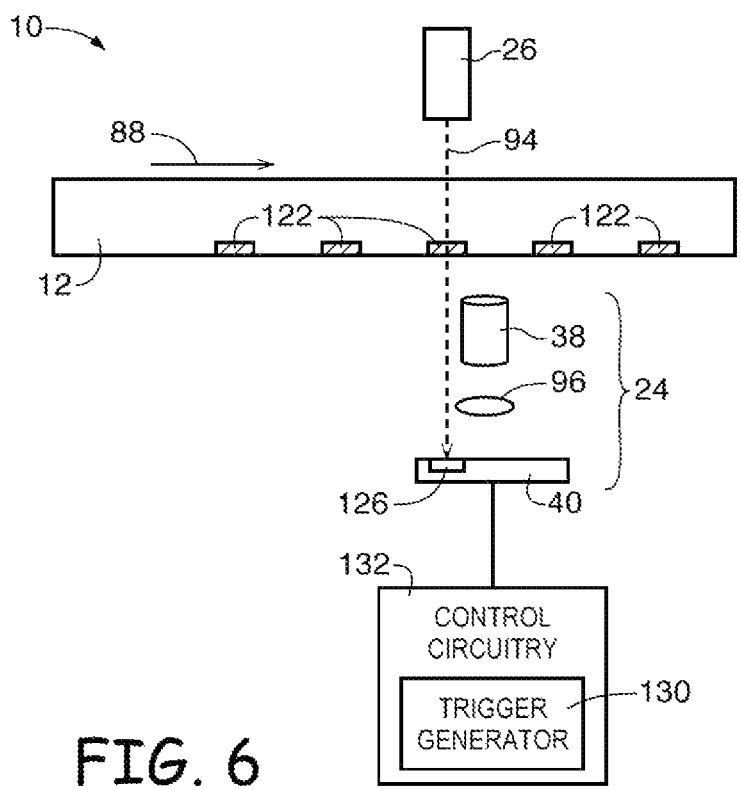
FIG. 6 is a diagram of an illustrative handheld diagnostic system that employs an automated image capture mechanism using a portion of an image sensor and a series of reference markings on a sample holder in accordance with an embodiment of the present invention.

Sensor 126 need not be separate from image sensor 40. If desired, a portion of pixel array 42 (FIG. 2) of image sensor 40 may be used to detect reference markings 122. A diagram illustrating how sensor 126 may be formed from a portion of image sensor 40 is shown in FIG. 6. As shown in FIG. 6, sensor 126 may be located on an edge of image sensor 40 and may be formed from a portion of pixel array 42 (e.g., one or more rows or columns of pixels in pixel array 42, one or more individual pixels or groups of pixels in pixel array 42, etc.).

Sensor 126 may be configured to detect when reference markings 122 pass through light 94 emitted by illumination module 26. Upon detecting one of reference markings 122, trigger generator 130 may generate a trigger signal for control circuitry 132, which may in turn issue control signals to image sensor 40 to capture an imaging frame. Thus, each time a reference marking 122 in sample holder 12 passes over sensor 126 at the edge of image sensor 40 in analysis module 14, image sensor 40 may capture an image of sample 80 in sample holder 12. This automated image capture mechanism ensures that imaging frames are captured at a uniform spatial distribution even when the sample is moving and even when the sample holder is inserted manually into the analysis module at variable speeds.

Figure 7:
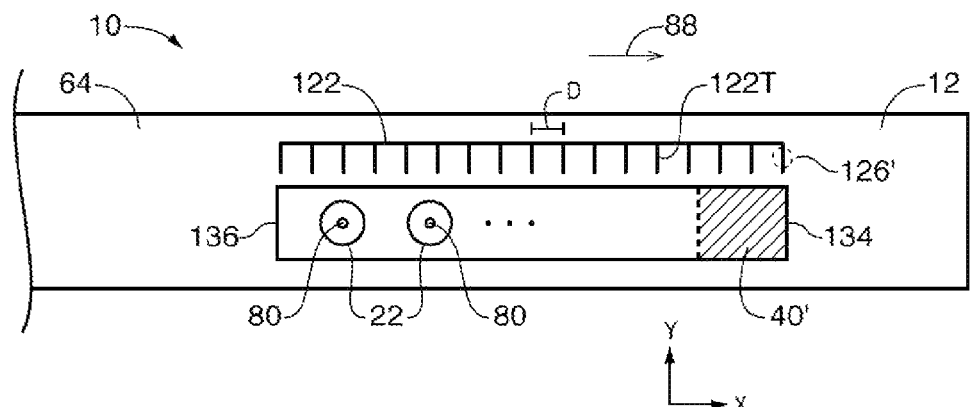
FIG. 7 is a top view of an illustrative sample holder having a series of reference markings for triggering an automated image capture mechanism in a handheld diagnostic system of the type shown in FIG. 5 in accordance with an embodiment of the present invention.

A top view of the arrangement of FIG. 5 is shown in FIG. 7. As shown in FIG. 7, reference markings 122 may pass through field of view 126' of sensor 126 as sample holder 12 is moved in direction 88. In response to one of tick marks 122T of reference markings 122 passing through field of view 126', control circuitry 132 may issue a control signal to image sensor 40 to capture an imaging frame. Region 40' indicates the field of view of image sensor 40 during an image capture. As a user inserts sample holder 12 into analysis module 14, tick marks 122T will each successively pass over sensor 126, and chip-scale microscope 24 will capture a corresponding series of imaging frames as test chambers 22 move across imaging frame region 40' from edge 134 to edge 136.

The rightmost edge of each imaging frame region 40' may be separated from the rightmost edge of the adjacent imaging frame region by a distance D (i.e., a distance corresponding to the separation between tick marks 122T). If desired, tick marks 122T may be spaced such that a region of overlap exists between adjacent imaging frames so that the images can be integrated as tiles to generate a larger field of view than chip-scale microscope 24 can achieve in a single imaging frame.

Figure 8:
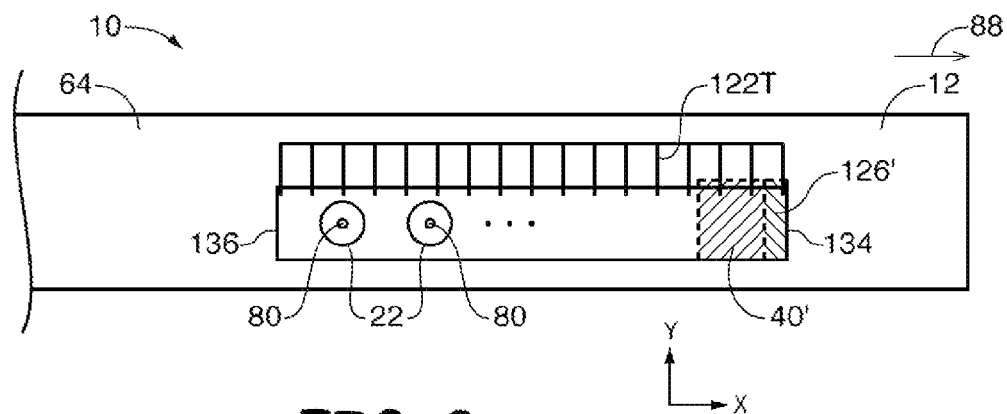
FIG. 8 is a top view of an illustrative sample holder having a series of reference markings for triggering an automated image capture mechanism in a handheld diagnostic system of the type shown in FIG. 6 in accordance with an embodiment of the present invention.

A top view of the arrangement of FIG. 6 is shown in FIG. 8. In this type of configuration, sensor 126 is formed from a portion of pixel array 42 (FIG. 2). In other words, a first portion of pixel array 42 is used to detect reference markings 122, while a second portion of pixel array 42 is used to capture images of sample 80 in sample holder 12. Region 126' indicates the field of view of sensor 126 at the edge of image sensor 40 and region 40' indicates the field of view of the portion of image sensor 40' that is used to capture images of sample 80. As shown in FIG. 8, reference markings 122 may pass through field of view 126' of sensor 126 as sample holder 12 is moved in direction 88. In response to one of tick marks 122T of reference markings 122 passing through field of view 126', control circuitry 132 may issue a control signal to image sensor 40 to capture an imaging frame. As a user inserts sample holder 12 into analysis module 14, tick marks 122T will each successively pass over sensor 126, and chip-scale microscope 24 will capture a corresponding series of imaging frames as test chambers 22 move across imaging frame region 40' from edge 134 to edge 136.

The rightmost edge of each imaging frame region 40' may be separated from the rightmost edge of the adjacent imaging frame region by a distance D (i.e., a distance corresponding to the separation between tick marks 122T). If desired, tick marks 122T may be spaced such that a region of overlap exists between adjacent imaging frames so that the images can be integrated as tiles to generate a larger field of view than chip-scale microscope 24 can achieve in a single imaging frame.

In the illustrative examples of FIGS. 7 and 8, tick marks 122T are formed along a line that is parallel to the length of sample imaging portion 64 of sample holder 12 (i.e., along the x-axis as shown in FIG. 7). This arrangement is merely illustrative. If desired, tick marks 122T may be formed along multiple axes such as both the x-axis and y-axis. Using a multiple-axes tracking system may be used to compensate for sample motion in multiple directions. Motion along each axis may be sensed independently by sensor 126 by using a unique color for each axial marking or by using other suitable identifying characteristic.

Figure 9:
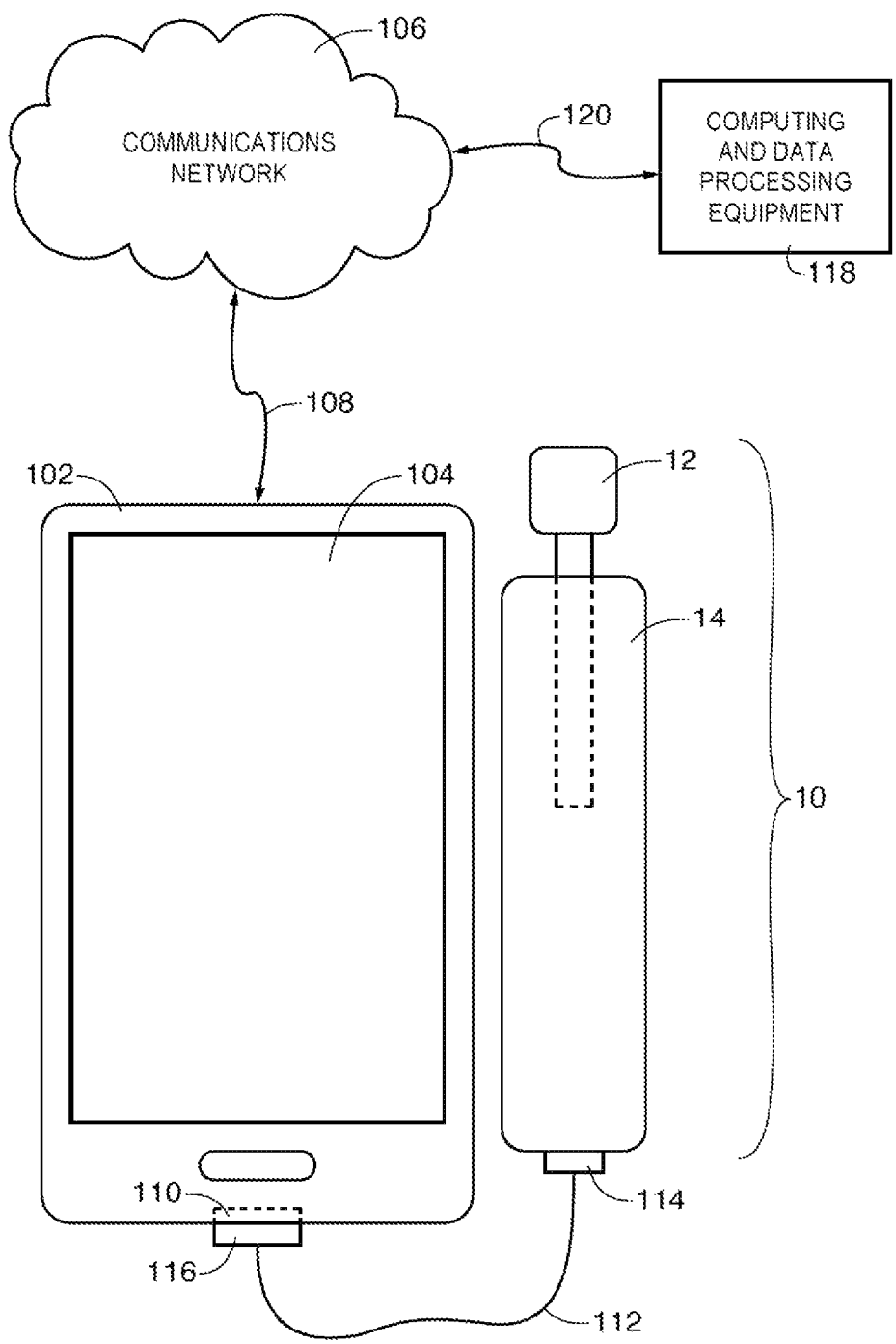
FIG. 9 is a diagram of an illustrative diagnostic system having a sample holder for containing a sample, an analysis module having a chip-scale microscope for capturing magnified images of the sample, and an electronic device for obtaining sample analysis information from the analysis module in accordance with an embodiment of the present invention.

FIG. 9 is a diagram showing how a handheld diagnostic system such as system 10 may be configured to communicate with computing equipment such as computing equipment 102. Computing equipment 102 may be a portable electronic device (e.g., a mobile phone, a personal digital assistant, a laptop computer, a tablet computer, or other computing equipment). Computing equipment 102 may include a display such as display 104 for presenting visual information to a user based on data received from system 10. For example, display 104 may be used in displaying images of samples acquired by system 10 (sometimes referred to as sample image data) and/or may be used in displaying sample analysis information (e.g., may present a list of bacteria, viruses, poisons, fungi, or parasites which were found present in the sample).

Computing equipment 102 may have a user input interface for gathering input from a user and for supplying output to a user. The user input interface may include user input devices such as keyboard, keypads, mice, trackballs, track pads, etc. If desired, display 104 may be touch-sensitive (i.e., display 104 may be a touch screen) and may be used to gather user input from a user. Computing equipment 102 may also include equipment for supplying output such as speakers for providing audio output, status indicator lights for providing visible output, etc.

Computing equipment 102 may include a data port such as data port 110. Data port 110 may be connected to analysis module 14 using a cable such as cable 112. On one end, cable 112 may have a connector such as connector 114 configured to mate with output port 34 of analysis module 14 (FIG. 4). On an opposing end, cable 112 may have a connector such as connector 116 configured to mate with data port 110 of computing equipment 102. Sample image data and/or sample analysis information may be conveyed from analysis module 14 to computing equipment 102 via cable 112. This is, however, merely illustrative. If desired, information may be conveyed from sample analysis module 14 to computing equipment 102 over a wireless network. As another example, data port 110 may be a Universal Serial Bus (USB) port and may be configured to receive output port 34 of analysis module 14 directly (without requiring cable 112).

Computing equipment 102 may be used to analyze sample image data and/or sample analysis information (e.g., to produce images of the sample from raw image data, to produce enhanced images of the sample, to analyze images of the sample to produce sample evaluation information or diagnosis information, etc.). Computing equipment 102 may, if desired, transmit data from system 10 to computing and data processing equipment 118 via communications network 106.

Communications network 106 may include wired and wireless local area networks and wide area networks (e.g., the internet).

Computing equipment 102 may be connected to network 106 using a link such as link 108 (e.g., a wired link that uses a modem or wireless link such as a local wireless link), and computing and data processing equipment 118 may be connected to network 106 using a link such as link 120 (e.g., a wired link that uses a modem or wireless link such as a local wireless link). Computing and data processing equipment 118 may be a remote mainframe computer, may be a cloud computing network (i.e., a network of computers on which software can be run from computing equipment 102) or other computing equipment. If desired, computing and data processing equipment 118 may be used to perform advanced analysis on sample image data and/or sample analysis information from system 10 (e.g., advanced analysis that requires more computing power than computing equipment 102 is capable of).

Figure 10:
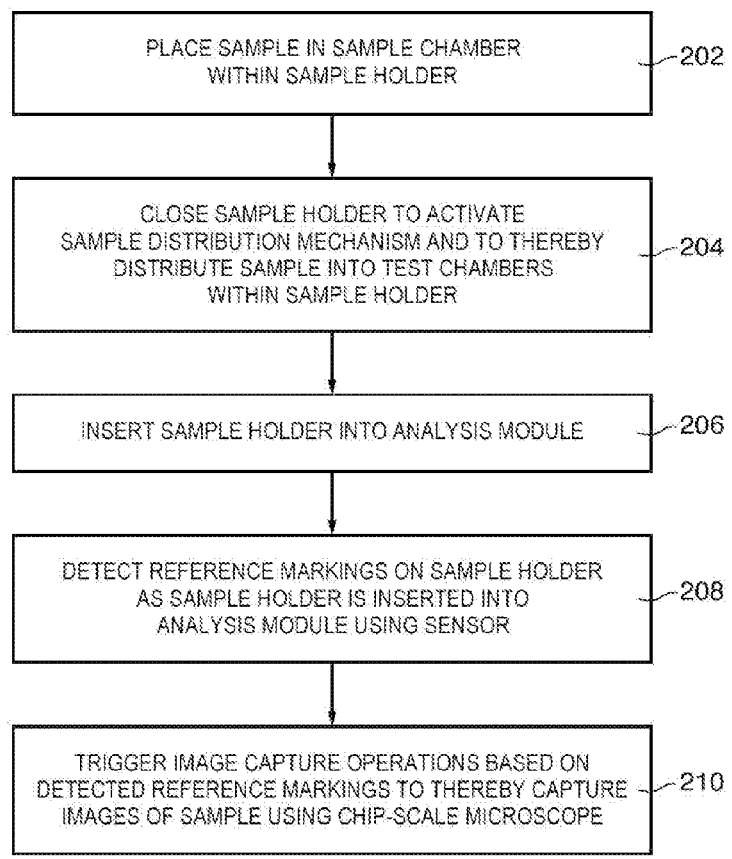
FIG. 10 is a flow chart of illustrative steps involved in operating a handheld diagnostic system of the type shown in FIGS. 1-9 in accordance with an embodiment of the present invention.

FIG. 10 is a flow chart of illustrative steps involved in using a system such as system 10 of FIGS. 1-9 in acquiring images of cells or other samples.

At step 202, a sample may be injected into a sample chamber in a sample holder such as sample chamber 16 in sample holder 12.

At step 204, the sample holder may be closed to automatically activate the sample distribution mechanism and thereby distribute portions of the sample from the sample chamber to respective test chambers in the sample holder. The sample distribution mechanism may be controlled by flow control components such as flow control components 20 of FIG. 3.

At step 206, a user may insert the sample holder into an analysis module such as analysis module 14 of FIG. 4 by inserting sample imaging portion 64 of sample holder 12 into opening 86 of analysis module 14.

At step 208, sensor 126 may detect reference markings 122 as they pass through its field of view during insertion of sample holder 12 into analysis module 14. In configurations where sensor 126 is separate from image sensor 40, a light source such as light source 124 may emit light towards sensor 126. Sensor 126 may detect each tick mark 122T by detecting a change in received light as the tick mark passes through the light emitted by light source 124. In configurations where sensor 126 is formed from a portion of image sensor 40 (e.g., from a portion of pixel array 42), sensor 126 may detect each tick mark 122T by detecting a change in received light as the tick mark passes through the light emitted by illumination module 26.

At step 210, trigger generator 130 may generate trigger signals for control circuitry 132 in response to sensor 126 detecting tick marks 122T. In response to each trigger signal, control circuitry 132 may issue control signals to chip-scale microscope 24 to capture an imaging frame. Multiple imaging frames may be captured of sample 80. Because imaging frame capture operations are triggered based on the detected reference markings, the imaging frames may have a uniform spatial distribution regardless of whether or not the user inserts sample holder 12 into analysis module 14 at a uniform speed. If desired, adjacent imaging frames may have some overlap with each other so that the imaging frames may be integrated as tiles to generate a large field of view image.

Various embodiments have been described illustrating a handheld diagnostic system for imaging and analyzing cells and other substances. The handheld diagnostic system may include a disposable sample holder for collecting a sample, safely containing the sample, and for presenting the sample to an analysis module having a chip-scale microscope.

The sample holder may include fluid control components for automatically distributing portions of the sample to respective test chambers in the sample holder for imaging. The test chambers may include markers (e.g., dyes, stains, fluorescence markers, etc.) configured to mark or otherwise identify specific nucleic acids or proteins in the sample if present in the sample. The test chambers may be located in a transparent portion of the sample holder The analysis module may have a housing with an opening. The opening may be configured to receive the transparent portion of the sample holder. While a user inserts the transparent portion of the sample holder into the opening of the analysis module, the chip-scale microscope may capture images of the sample in each test chamber as each test chamber passes through the field of view of the chip-scale microscope.

The analysis module may include an interchangeable illumination module for illuminating the sample and a chip-scale microscope for capturing images of the sample. The chip-scale microscope may include an image sensor having an array of image pixels configured to gather pixel data from the sample. The chip-scale microscope may also include optics such as one or more objective lenses for gathering light from the sample and focusing the light onto the image sensor.

The analysis module may include storage and processing circuitry for processing pixel data and, if desired, analyzing the processed pixel data to produce sample analysis information. The pixel data and/or the sample analysis information may be transmitted to external computing equipment such as a portable electronic device for further analysis and/or for displaying sample analysis information for a user based on the sample images acquired using the chip-scale microscope.

The chip-scale microscope may be configured to capture spatially uniform imaging frames using an automated image capture mechanism. The automated image capture mechanism may be based on a sensor that detects when the next imaging frame should be captured. For example, the sample holder may include a series of uniformly spaced markings. When a user inserts the sample holder into the analysis module, the series of uniformly spaced markings may be detected by a sensor in the analysis module. Upon detecting one of the markings, a control signal may be issued to capture an imaging frame using the chip-scale microscope. This type of automated triggering ensures that the chip-scale microscope captures imaging frames at uniform spatial distribution even when the sample is moving and even when the sample holder is inserted manually into the analysis module at variable speed. The sensor may be a photodiode that is separate from the image sensor in the chip-scale microscope or may formed from one or more image pixels at an edge of the image sensor in the chip-scale microscope.

The foregoing is merely illustrative of the principles of this invention which can be practiced in other embodiments.

What is claimed is:

1. A handheld sample holder, that is insertable into a chip-scale microscope, the handheld sample holder comprising:
    a sample-receiving portion including a sample chamber configured to receive a biological sample, the sample receiving portion also including an outer surface thereof;
    a transparent sample imaging portion including a plurality of test chambers, wherein each test chamber is coupled to the sample chamber by a channel;
    flow control components configured to generate pressure that moves the biological sample through the channel and distributes a respective portion of the biological sample to each of the plurality of test chambers; and a plurality of uniformly spaced reference marks on the outer surface of the sample imaging portion, wherein the reference marks are each configured to trigger the chip-scale microscope to capture an image of the biological sample in the transparent sample imaging portion of the handheld sample holder when the handheld sample holder is inserted into the chip-scale microscope.

2. The handheld sample holder defined in claim 1 wherein the sample imaging portion has a length, wherein the test chambers are located in the sample imaging portion and are configured to be imaged with a chip-scale microscope, and wherein the reference marks are located along the length of the sample imaging portion.

3. The handheld sample holder defined in claim 1 wherein the flow control components comprise a first chemical reactant and a second chemical reactant that are configured to produce gas when the first chemical reactant is mixed with the second chemical reactant.

4. The handheld sample holder defined in claim 1 wherein the sample-receiving portion has a clamshell shape and is configurable in open and closed positions, and wherein the flow control components are activated by placing the sample-receiving portion in the closed position.

5. The handheld sample holder defined in claim 1, wherein the reference marks are positionally located relative to each of the plurality of test chambers to allow an external image capture device to capture images of the test chambers.

6. The handheld sample holder defined in claim 1, wherein the reference marks are positioned along a single axis.

7. The handheld sample holder defined in claim 1, wherein the reference marks are positioned along at least two different axes.

8. The handheld sample holder defined in claim 7, wherein the axes are orthogonal to each other.

9. The handheld sample holder defined in claim 8, wherein the reference marks are positionally located relative to each of the plurality of test chambers to allow an external image capture device to capture images of the test chambers.

* * * * *